US012791453B2

(12) United States Patent
Schmieder

(10) Patent No.: US 12,791,453 B2
(45) Date of Patent: Nov. 10, 2026

(54) DEVICE AND METHOD FOR SEPARATING PARTICLES OF DIFFERENT SIZES IN A LIQUID, AND APPLICATIONS OF THE DEVICE

(71) Applicant: FRAUNHOFER-GESELLSCHAFT ZUR FÖRDERUNG DER ANGEWANDTEN FORSCHUNG E.V., Munich (DE)

(72) Inventor: Florian Schmieder, Dresden (DE)

(73) Assignee: Fraunhofer-Gesellschaft zur förderung der angewandten Forschung e.V., Munich (DE)

( * ) Notice: Subject to any disclaimer, the term of this patent is extended or adjusted under 35 U.S.C. 154(b) by 456 days.

(21) Appl. No.: 18/259,185

(22) PCT Filed: Dec. 23, 2021

(86) PCT No.: PCT/EP2021/087577

§ 371 (c)(1),
(2) Date: Jun. 23, 2023

(87) PCT Pub. No.: WO2022/144314

PCT Pub. Date: Jul. 7, 2022

(65) Prior Publication Data

US 2024/0053237 A1 Feb. 15, 2024

(30) Foreign Application Priority Data

Dec. 28, 2020 (DE) ..................... 10 2020 216 578.5

(51) Int. Cl.
*G01N 1/40* (2006.01)
*G01N 33/49* (2006.01)

(52) U.S. Cl.
CPC ......... *G01N 1/4077* (2013.01); *G01N 33/491* (2013.01); *G01N 2001/4083* (2013.01); *G01N 2001/4088* (2013.01)

(58) Field of Classification Search
None
See application file for complete search history.

(56) References Cited

U.S. PATENT DOCUMENTS 3,972,812 A 8/1976 Gresl, Jr.
6,139,757 A 10/2000 Ohmura et al.
6,312,950 B1 11/2001 Ohmura et al.

FOREIGN PATENT DOCUMENTS

EP 0 502 213 B1 3/2003
JP S51-024979 A 2/1976

(Continued)

OTHER PUBLICATIONS

Alternate machine translation of JP 2007-175596 published Jul. 12, 2007.*

(Continued)

*Primary Examiner* — Daniel S Larkin
(74) *Attorney, Agent, or Firm* — Leydig, Voit & Mayer, Ltd.

(57) ABSTRACT

The invention relates to a device and a method for separating particles of different sizes in a liquid. The invention additionally relates to applications of the device according to the invention. The device according to the invention and the method according to the invention involve the capability of modifying the diameter of the pores of the at least one filter element of the device in a controlled manner (e.g., the pore diameter can be increased or decreased). The device and method have the advantage that particles of different sizes (e.g., biological cells and/or endosomes) of a liquid can be separated from one another with a high degree of separation efficiency, and the particles are separated in a simple, quick, (Continued)

Figure 1:
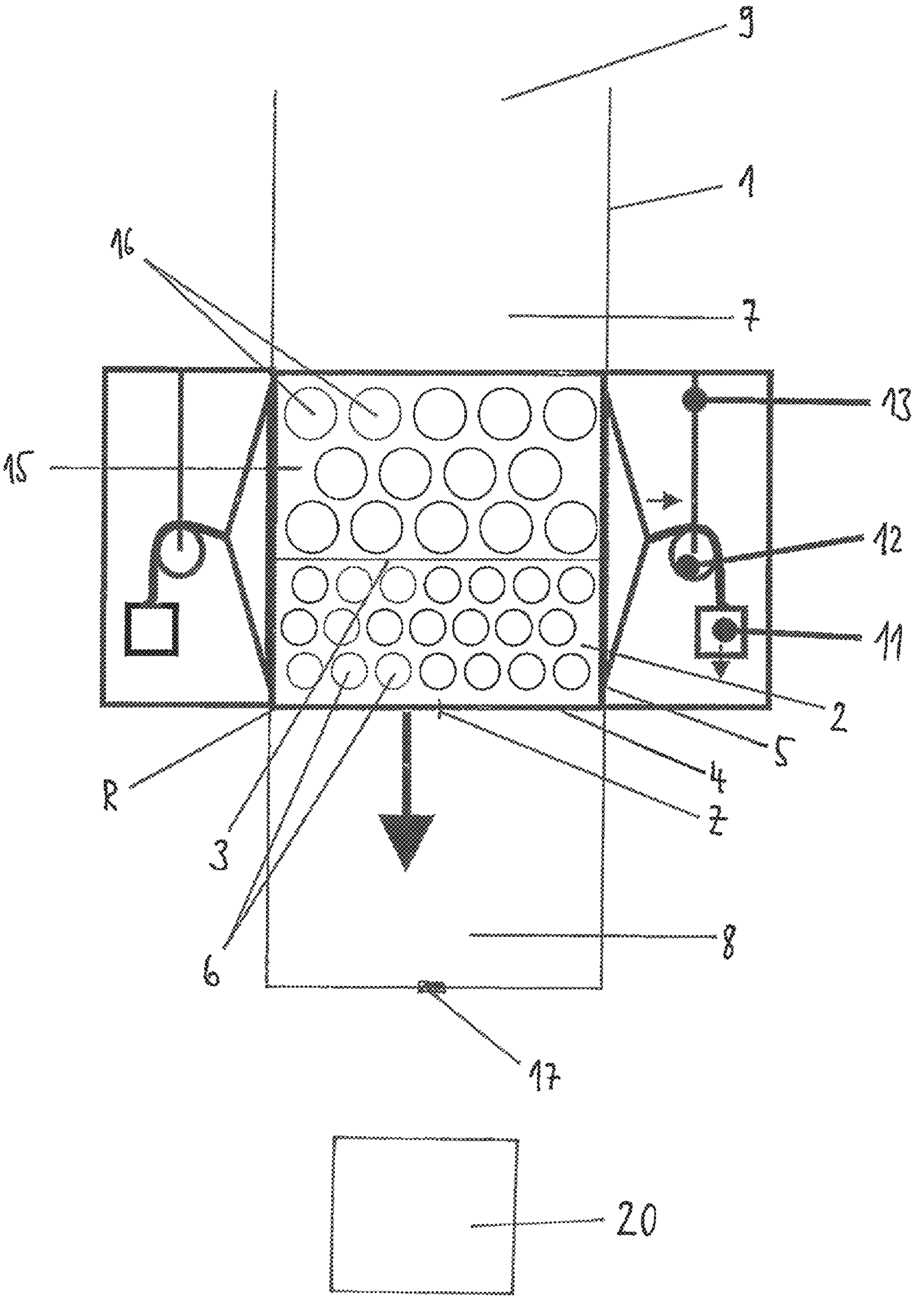

and inexpensive manner. High yields can be produced, and the separated particles can be provided in a therapeutically applicable liquid (e.g., blood plasma).

16 Claims, 4 Drawing Sheets

(56) References Cited

FOREIGN PATENT DOCUMENTS

| | | | |
|---|---|---|---|
| JP | H10-137557 | A | 5/1998 |
| JP | 2000-083649 | A | 3/2000 |
| JP | 2007-175596 | A | 7/2007 |
| JP | 2008-168176 | A | 7/2008 |
| WO | WO 2015/192020 | A1 | 12/2015 |

OTHER PUBLICATIONS

Canadian Intellectual Property Office, First Examination Report in Canadian Patent Application No. 3,206,314 (Dec. 3, 2025).
Japan Patent Office, Notification of Reasons for Refusal in Japanese Patent Applicatoin No. 2023-539332 (Oct. 21, 2025).
German Patent Office, Examination Report in German Patent Application No. 10 2020 216 578.5 (Nov. 10, 2021).
European Patent Office, International Search Report in International Application No. PCT/EP2021/087577 (Apr. 11, 2022).
European Patent Office, Written Opinion in International Application No. PCT/EP2021/087577 (Apr. 11, 2022).
International Bureau of WIPO, International Preliminary Report on Patentability in International Application No. PCT/EP2021/087577 (Jul. 4, 2023).

* cited by examiner

DEVICE AND METHOD FOR SEPARATING PARTICLES OF DIFFERENT SIZES IN A LIQUID, AND APPLICATIONS OF THE DEVICE

CROSS-REFERENCE TO RELATED APPLICATIONS

This patent application is the U.S. national phase of International Application No. PCT/EP2021/087577, filed on Dec. 23, 2021, which claims the benefit of German Patent Application No. 10 2020 216 578.5, filed Dec. 28, 2020.

A device and a method for separating differently sized particles in a liquid are provided. Furthermore, uses of the device according to the invention are provided. The device according to the invention and the method according to the invention are based on the fact that the pore diameter of the pores of the at least one filter element of the device can be deliberately changed (for example, increased or decreased). The device and the method have the advantage that differently sized particles (for example, biological cells and/or endosomes) of a liquid can be separated from one another with high selectivity, and the separation of the particles is carried out easily, rapidly and cost-effectively, wherein high yields can be achieved, and the separated particles can be provided in a therapeutically usable liquid (for example, blood plasma).

The separation of differently sized particles in a liquid (for example, a biosuspension containing biological cells and/or pathogens) is of great interest for a large number of issues in medical technology (for example, obtaining blood cell products, the laboratory analysis of individual constituents and/or the treatment of cell products for cell therapeutic measures).

Two fundamental principles for separation have become particularly well-established. The first fundamental principle separates particles present in a liquid based on the differing specific densities thereof or based on the differing mechanical properties thereof (for example, the deformability and/or orientation thereof in a flow of liquid). In general, filtration and/or centrifugation are used for this purpose. The second fundamental principle separates particles based on the differing surface properties thereof. In the case of cells, viruses and/or endosomes as particles, these differing surface properties are caused by the exposure of differing molecules (for example, proteins, lipids and/or sugar) at the surfaces of these particles.

Devices and methods for separating differently sized particles in a liquid from one another are already known in the prior art.

First, centrifugation is known. This is used, for example, for purifying whole blood, essentially for producing blood products for therapeutic use. A distinction is made between different types of separation, wherein these are always composed of a succession of multiple centrifugation steps. Whole blood is usually centrifuged directly in the blood collection bag and distributed in a separate machine among further bags, which are connected to this bag by way of hoses. The end products are erythrocytes (so-called "packed RBCs"), platelet-rich or platelet-poor blood plasma, thrombocytes and peripheral blood monocular cells (so-called "PBMCs"). The greatest disadvantage of this established method is the low purity of the end products that are achieved, in particular of the PBMCs, which are present in the so-called "buffy coat."

Secondly, density gradient centrifugation is known. Density gradient centrifugation of whole blood is essentially used, for example, in the diagnostic field. This is due to the fact that the separation medium used with this method cannot be completely separated at the end of the method, which renders the provided, separated cell suspensions unsuitable for therapeutic use. In generally, the method takes place similarly to centrifugation. Prior to this method, however, a separation medium is underlayered beneath the blood, the density of which is between the density of the PBMCs and that of the erythrocytes and granulocytes. As a result, a separation phase arises during separation between an erythrocyte/granulocyte phase and a PBMC phase, which enables enhanced separation of the PBMCs. The desired end product of the separation is usually the PBMCs. The disadvantages of the method are the lack of purity of the end products, the poor yield as well as the complicated handling when pipetting off the cells.

Third, microfluidic separation by way of microarrays is known. In these methods, separation of blood cells is achieved by way of a flow of the blood cell suspension through a micromesh, which is integrated into a microfluidic cartridge. Using such cartridges, it is possible to achieve high purities with respect to the separation of PBMCs. The disadvantages of this method, however, are the complicated activation and a very long process duration (the duration of separation by way of microfluidics is approximately 3 hours for 400 mL whole blood).

Fourth, plasma apheresis is known, which represents centrifugation in a continuous process. During blood collection, blood is continuously mixed with anticoagulants and pumped by a pump into a rotating centrifugation vessel. The cells separated from the plasma are collected, isotonically balanced with physiological salt solution, and subsequently returned to the patient via a further pump. The greatest disadvantage of the method is that only two fractions of the blood can be continuously separated, and thus no fine division into more than two cell fractions can be carried out.

Fifth, filtration is known. These methods usually utilize either a filter membrane for plasma separation or a filter membrane for separating cell fractions, such as PBMCs. The filter membrane that is used is ideally installed directly in a vessel so as to collect liquid including the particles that pass through the membrane. Moreover, separation vessels are known, in which a cascade of filters is used to isolate differing fractions from one another. Furthermore, a method is known in which cells are enclosed in microcubes by introducing porous microcubes into the suspension. The presently known filtration methods have the disadvantage that only very coarse separation of particles of a liquid is possible, that is, ultimately only two types of particles can be separated from one another, namely particles having a diameter smaller than a pore diameter of the pores of the filter membrane from particles having a diameter larger than a pore diameter of the pores of the filter membrane. So as to achieve higher selectivity, further measures must be taken (for example, absorption of certain particles in microcubes), which are time-consuming and cost-intensive and decrease the yield of separated cells.

Proceeding from this, it was the object of the present invention to provide a device and a method for separating differently sized particles in a liquid which do not have the disadvantages of the prior art. In particular, it should be made possible by way of the device and the method to separate differently sized particles (for example, biological cells and/or endosomes) of a liquid from one another with high selectivity, and to provide separated particles easily, rapidly and cost-effectively in high yield and in a therapeutically usable liquid. Moreover, uses of the device should be proposed.

The object is achieved by the features of the device and method described herein, and the advantageous embodiments thereof. Uses according to the invention are also described.

According to the invention, a device for separating differently sized particles in a liquid is provided, comprising:

a) a receptacle for receiving a liquid;

b) at least one filter element, having a top surface, a bottom surface, and at least one side surface connecting the top surface to the bottom surface, the filter element including through-pores having a defined pore diameter, the filter element being arranged in the receptacle so as to divide the receptacle, in the direction of the top surface of the filter element, into an upper compartment and, in the direction of the bottom surface of the filter element, into a lower compartment, so that particles of a liquid in the upper compartment can only reach the lower compartment if they pass through the filter element, the upper compartment of the receptacle having an opening for receiving a liquid including particles, characterized in that the device comprises a means for changing the pore diameter of the pores of the filter element.

The device according to the invention has the advantage that differently sized particles (for example, biological cells and/or exosomes/endosomes) of a liquid can be separated from one another with high selectivity. The high selectivity is provided by the means of the device which is suitable for changing the pore diameter of the pores of the filter element. Using this means, it is possible to deliberately change (that is, in particular increase) the pore diameter over the course of a separation process so as to consecutively allow particles having differing particle sizes (that is, in particular, smaller particles first, and then larger particles) to pass through the filter element. The device thus enables a chronological succession of the release of the differing particles into the lower compartment of the receptacle of the device. Prior to each change of the pore diameter of the filter element, the respective liquid including the passed particles can be removed from the lower compartment so that, at the end of the separation process, several separate liquids are present, which differ in that these contain particles having differing particle diameters. It is possible to change the pore diameter not only incrementally, but linearly, so that very high selectivity can be achieved by way of the device.

Furthermore, the particles of the starting liquid can be separated easily, rapidly and cost-effectively from one another in high yield. The ease, rapid speed and low costs result from the fact that only a single device is used for separating the particles of the liquid, that is, it is not necessary to use several different devices one after another to achieve the separation of the particles. This also results in a higher yield of particles since the particles come in contact with fewer surfaces during the separation process thereof, on which they could otherwise adsorb. This also achieves that the separation method can be carried out very rapidly using the device according to the invention since cleaning steps for further devices can be dispensed with. The device can moreover be provided in a cost-effective manner since it is composed of components that are not expensive. The scalability of the device is another advantage, that is, the suitability of the device, when the receptacle (in particular the upper compartment thereof) is accordingly enlarged, to receive liquids with a very large volume and separate the particles thereof according to size.

It is a further advantage of the device that the particles, after having been separated, can be present in the soluble fraction of the starting liquid thereof. In other words, it is possible, using the device, for the soluble fraction of the starting liquid, in which the differently sized particles are present at the start of the separation process, to remain unchanged at the end of the separation process. If blood serves as the starting liquid including particles, that is, if blood plasma as starting liquid including blood cells and exosomes as particles, this is a crucial advantage since the separated particles can then be present in blood plasma. Blood plasma represents a therapeutically usable liquid since the liquid is suitable for transfusions, for example.

The device can be characterized in that the means for changing the pore diameter of the pores of the filter element is suitable for exerting a force on the filter element, which is either directed from the center of a surface of the filter element toward the edges of this surface of the filter element, or in the opposite direction. The pore diameter of the pores of the filter element can be increased or decreased by the action of such a force.

The means for changing the pore width of the pores of the filter element can comprise a centrifuge and include at least one body that is connected to an outer side of the at least one side surface of the filter element in a force-fit manner, or includes at least two bodies, each of which is connected to an outer side of two opposing side surfaces of the filter element in a force-fit manner. The at least one body is characterized by being suitable for exerting a compression force or tensile force on the at least one side surface of the filter element by way of a change of the rotational speed of the centrifuge, so that the pores of the filter element are compressed or expanded. The mechanism of action of this means is therefore based on tensile action or compressive action acting on the side surface of the filter element, which occurs as a function of gravity, which, in turn, can be adjusted by way of the rotational speed of the centrifuge. Such a means allows the pore diameter to be adjusted more rapidly and more easily than, for example, when using a means by way of which the pore diameter is achieved by exerting mechanically adjustable pressure on the at least one filter element (for example, exertion of pressure on the at least one filter element which can be adjusted mechanically by way of screws of a clamping device).

Furthermore, the means for changing the pore width of the pores of the filter element can comprise a centrifuge and include at least one body, preferably several bodies, which are arranged at the top side of the filter element and/or in the filter element and which particularly preferably have a higher specific density and/or a higher electric charge than the particles to be separated. The at least one body is, preferably the several bodies are, particularly preferably embodied as nanoparticles, wherein the nanoparticles are in particular arranged around the pores of the filter element. The at least one body is characterized by being suitable for exerting a compression force or tensile force on the pores of the filter element by way of a change of the rotational speed of the centrifuge, so that the pores of the filter element are compressed or expanded. The mechanism of action of this means is thus based on tensile action or compressive action that is present as a function of the gravity acting locally on the pores of the filter element. The level of the force of gravity can also be adjusted here by way of the rotational speed of the centrifuge. Such a means allows the pore diameter to be adjusted more rapidly and more easily than, for example, when using a means by way of which the pore diameter is achieved by exerting mechanically adjustable pressure on the at least one filter element (for example, exertion of pressure on the at least one filter element which can be adjusted mechanically by way of screws of a clamping device). The advantage of this embodiment compared to the above-described embodiment is that the at least one body is partially arranged within the receptacle, and the device can thus have a more compact design than when the at least one body is connected to an outer side of the at least one side surface of the filter element in a force-fit manner.

Apart from this, the means for changing the pore width of the pores of the filter element can comprise an electrical voltage source and can comprise at least one electrically conductive layer, optionally at least two electrically conductive layers, wherein the electrical voltage source is connected to the at least one electrically conductive layer, optionally to the at least two electrically conductive layers, in an electrically conducting manner, wherein the at least two electrically conductive layers are preferably arranged at two opposing surfaces of the at least one side surface of the filter element and electrically insulated with respect to one another. The electrical voltage source is characterized by being suitable for exerting a compression force or tensile force on the at least one electrically conductive layer, optionally the at least two electrically conductive layers, by way of a change of the electrical voltage, so that the pores of the filter element are compressed or expanded. Such a means allows the pore diameter to be adjusted more rapidly and more easily than, for example, when using a means by way of which the pore diameter is achieved by exerting mechanically adjustable pressure on the at least one filter element (for example, exertion of pressure on the at least one filter element which can be adjusted mechanically by way of screws of a clamping device). In this embodiment, the device can comprise a centrifuge. One advantage is that the particles in the liquid can be separated more rapidly than by mere gravity since the centrifugal force of the centrifuge accelerates the passing of the liquid and of the particles through the at least one filter element. The electrical voltage source can be configured to apply an electrical voltage in the range of 500 to 4000 V to the at least one electrically conductive layer, optionally the at least two electrically conductive layers.

In this embodiment, the filter element preferably comprises or consists of an electroactive material and/or a piezoelectric material, which has through-pores. Particularly preferably, the material comprises or consists of an electroactive polymer and/or piezoelectric polymer, in particular a magnetorheological elastomer and/or piezoelectric elastomer. This may be an elastomer (for example, selected from the group consisting of silicone elastomer, thermoplastic elastomer, and combinations thereof) that contains embedded magnetic and/or piezoelectric nanoparticles. According to the invention, the term "nanoparticles" shall be understood to mean particles having a diameter of 1 nm to 100 μm, measured by electron microscopy. The understanding according to the invention of the term "nanoparticles" thus also encompasses "microparticles" when a diameter of 1 μm to 100 μm is assumed for the term "microparticles." The magnetic and/or piezoelectric particles can be selected from the group consisting of lithium niobate, lithium tantalate, and combinations thereof.

In a preferred embodiment, the device comprises a control unit, which is configured to control the means for changing the pore diameter of the pores of the filter element.

The control preferably takes place in such a way that a centrifugal speed of a centrifuge of the means for changing the pore diameter of the pores of the filter element is changed, preferably in such a way that the centrifugal speed is incrementally increased over the course of the separation of particles in a liquid, wherein the increase in particular takes place automatically over time or manually by input of a user.

The control unit can furthermore be configured to control the means for changing the pore diameter of the pores of the filter element in such a way that an electrical voltage of a voltage source of the means for changing the pore diameter of the pores of the filter element is changed, preferably in such a way that the electrical voltage is incrementally decreased over the course of the separation of particles in a liquid, wherein the decrease in particular takes place automatically over time or manually by input of a user.

The control unit can additionally be configured to control the means for changing the pore diameter of the pores of the filter element in such a way that the pore diameter of the pores of the filter element is changed in a range of 100 nm to 100 μm. A pore diameter in this range is advantageous for separating blood particles, that is, for separating blood cells and exosomes occurring in the blood.

In addition, the control unit can be configured to control the means for changing the pore diameter of the pores of the filter element in such a way that the pore diameter of the pores of the filter element is incrementally changed, automatically over time or manually by input(s) of a user of the device, to a larger diameter, preferably from a pore diameter of 200 nm to a pore diameter of 20 μm and larger, particularly preferably from a pore diameter of 200 nm (advantageously for retaining exosomes) over a pore diameter of 3 μm (advantageously for retaining thrombocytes), a pore diameter of 4-7 μm (advantageously for retaining erythrocytes), a pore diameter of 8-12 μm (advantageously for retaining PBMCs), a pore diameter of 20 μm (advantageously for retaining macrophages, tissue cells and circulating tumor cells) to a pore diameter of 100 μm (to also allow the macrophages, tissue cells and circulating tumor cells to pass, preferably incrementally).

In a preferred embodiment, the device includes n further filter elements, which are arranged on the at least one filter element in the direction of the upper compartment of the receptacle and which in each case have through-pores having a defined pore diameter, wherein the defined pore diameter of the n filter elements is larger than the defined pore diameter of the at least one filter element and is larger for each of the n filter elements the closer the respective filter element is located in the direction of the upper compartment of the receptacle, wherein n is preferably an integer ≥2, particularly preferably an integer ≥3, and in particular an integer in the range of 4 to 10. With the exception of the diameter of the pores, each of the n further filter elements can have one, more or all properties of the at least one filter element of the device. The n further filter elements create a so-called "deep-bed filter," that is, a filter in which particles of the liquid can be retained, according to the size thereof, in certain of the n filter elements, that is, are not able to reach a filter element arranged further in the direction of the lower compartment. The advantage of this "deep-bed filter" is that clogging of the pores of the filter element can be avoided.

The device can comprise at least one second filter element, which is arranged on the filter element in the direction of the upper compartment of the receptacle and has through-pores having a second, defined pore diameter that is larger than the pore diameter of the filter element. With the exception of the diameter of the pores, the at least one second filter element can have one, more or all properties of the at least one filter element of the device. Prior to the pore diameter of these two filter elements being increased, a first group of smaller particles can, for example, be arranged in the at least one (=lower) filter element, and a second group of (larger) particles can be arranged in the second (=upper) filter element. Only after a corresponding increase of the pore diameter can the particles of the second group pass through the at least one filter element so as to ultimately reach the lower compartment of the device.

Optionally, the device can comprise at least one third filter element, which is arranged on a side of the second filter element which faces away from the filter element and has through-pores having a third, defined pore diameter that is larger than the pore diameter of the second filter element. With the exception of the diameter of the pores, the at least one third filter element can have one, more or all properties of the at least one filter element of the device. The additional third filter element intensifies the "deep-bed filter." Prior to the pore diameter of these three filter elements being increased, a first group of small particles can be arranged in the at least one filter element, a second group of larger particles can be arranged in the second filter element, and a third group of even larger particles can be arranged in the third filter element. Only after a corresponding increase of the pore diameter can the particles of the second group pass through the at least one filter element, and optionally the particles of the third group pass can pass through the second filter element (optionally also through the at least one filter element), so as to ultimately reach the lower compartment of the device. The advantage of avoiding clogging of the pores of the filter element is even more pronounced in this embodiment.

The at least one filter element, preferably each filter element, of the device preferably comprises or consists of fibers that have through-pores.

The at least one filter element, preferably each filter element, of the device preferably comprises or consists of an elastic material, preferably an elastic polymer having through-pores.

Furthermore, it is preferred for the at least one filter element, preferably each filter element, of the device to comprise or consist of an electroactive material, preferably an electroactive polymer, having through-pores. The advantage is that the pore diameter of the filter element can be controlled by the application of an electrical voltage, which allows rapid and fine adjustment of the pore diameter.

Apart from this, the at least one filter element, preferably each filter element, of the device can comprise or consist of a piezoelectric material having through-pores. The advantage is that the pore diameter of the filter element can be controlled by the application of an electrical voltage, which allows rapid and fine adjustment of the pore diameter.

The at least one filter element, preferably all filter elements, of the device can comprise or consist of a material that is selected from the group consisting of silicone elastomer, thermoplastic elastomer (TPE), magnetorheological elastomer, piezoelectric elastomer, thermoplastic urethane (TPU), and combinations thereof.

Furthermore, the at least one filter element, preferably all filter elements, of the device can comprise or consist of a composite material that preferably comprises or consists of an elastomer and (for example, magnetic, piezoelectric and/or gravitation-sensitive) nanoparticles embedded therein. The advantage is that, in the case of magnetic and/or piezoelectric particles (nanoparticles), the pore diameter of the filter element can be controlled by the application of an electrical voltage, and in the case of gravitation-sensitive nanoparticles, it can be controlled by the application of an acceleration force (for example, centrifugal force). In these cases, rapid and fine adjustment of the pore diameter is possible. According to the invention, the term "gravitation-sensitive" shall in particular be understood to mean that the particles have a specific density of ≥2 g/cm$^3$. According to the invention, the term "nanoparticles" shall be understood to mean particles having a diameter of 1 nm to 100 μm, measured by electron microscopy (that is, this understanding also encompasses "microparticles" when a diameter of 1 μm to 100 μm is assumed for the term "microparticles"). The gravitation-sensitive nanoparticles can be selected from the group consisting of metal particles, coated metal particles (for example, metal particles coated with a ceramic material), ceramic particles, and combinations thereof.

Furthermore, the at least one filter element, preferably all filter elements, of the device can comprise or consist of a woven fabric or knitted fabric made of fibers. The material of the woven fabric and/or knitted fabric does not have to have elastic properties (at the molecular level). The material of the woven fabric and/or knitted fabric can be selected from the group consisting of PES, PET, PC, PMMA, COC, nylon, glass fibers, PVDF, PP, and combinations thereof.

Apart from this, the at least one filter element, preferably all filter elements, of the device can comprise or consist of a material that is embodied as (asymmetrical) solid foam. If several filter elements are present, it is preferred for the several filter elements to comprise or consist of a solid foam, wherein particularly preferably the differing pore sizes of the individual filter elements steadily transition into one another within the solid foam, and thus only theoretical layers of the individual filter elements exist in the foam. The material of the solid foam can be selected from the group consisting of silicon elastomer, thermoplastic elastomer (TPE), magneto-rheological elastomer, piezoelectric elastomer, thermoplastic urethane (TPU), and combinations thereof. Furthermore, the material of the solid foam can comprise or consist of a composite material that preferably comprises or consists of an elastomer and (for example, magnetic, piezoelectric and/or gravitation-sensitive) nanoparticles embedded therein. Apart from this, the material of the solid foam can be selected from the group consisting of PES, PET, PC, PMMA, COC, nylon, glass fibers, PVDF, PP, and combinations thereof.

In addition, the at least one filter element, preferably each filter element, of the device can have an expansion from the top side thereof to the bottom side thereof of >250 μm, preferably of ≥500 μm, particularly preferably of ≥1 mm, most particularly preferably of ≥2 mm, in particular in the range of 3 mm to 10 mm.

The at least one filter element, preferably each filter element, of the device can comprise a coating that is suitable for reversibly binding certain particles of a liquid. The coating preferably comprises or consists of a material that is suitable for being influenced by the means for changing the pore diameter of the pores of the filter element in such a way that the bond with the certain particles is dissolved. Most particularly preferably, the material comprises or consists of an electroactive material, in particular an electroactive polymer.

Furthermore, the coating is preferably arranged at the top surface, bottom surface and/or pore inner surface of the at least one filter element, particularly preferably at a top surface, bottom surface and/or pore inner surface of all filter elements of the device. The advantage of the coating is that it is possible to retain certain particles regardless of size, and subsequently to selectively release such particles (in particular particles having a very small particle diameter). In this way, the selectivity can be further increased, and in particular particles having very small particle diameters can be separated more reliably.

The lower compartment of the receptacle of the device can comprise a means for withdrawing liquid from the lower compartment, preferably a valve, particularly preferably an acceleration-sensitive valve and/or a voltage-switchable valve. In particular, a control unit of the device can be configured to open and close the means for withdrawing the liquid automatically over time, or manually by input(s) of a user. It is of advantage that, over the course of the separation process, a liquid including particles that, in each case after the pore diameter of the filter element has changed, is present in the lower compartment can be isolated, that is, removed from the lower compartment. The removal of these respective liquids can take place deliberately by applying a certain acceleration and/or electrical voltage to the valve and/or can take place manually or automatically. Automatic removal is associated with less effort for the user, and is therefore more convenient and less susceptible to errors.

The receptacle of the device can be selected from the group consisting of centrifuge tubes, blood collection syringes, blood donation bags, culture bags for the biotechnological production of pharmaceuticals, bioreactor for biotechnological production, sample vessel, culture vessel, and combinations thereof.

The particles for the separation of which the device is suited can be selected from the group consisting of vesicles, virus particles and biological cells, preferably selected from the group consisting of vesicles, virus particles and biological cells from blood, particularly preferably selected from the group consisting of endosomal vesicles, exosomal vesicles (exosomes), virus particles, liposomes, thrombocytes, erythrocytes, leukocytes, and combinations thereof.

According to the invention, furthermore a method for separating differently sized particles in a liquid is provided, comprising the following steps:

a) providing a device according to the invention;
b) adjusting the pore diameter of the pores of the filter element of the device so that either no particles or only particles up to a desired particle diameter pass through the filter element;
c) filling the upper compartment of the receptacle of the device with a liquid containing particles having differing sizes;
d) moving the liquid through the filter element, preferably by way of a means selected from the group consisting of centrifuge, pump, and combinations thereof;
e) isolating the liquid, which optionally contains passed particles, from the lower compartment of the receptacle of the device;
f) increasing the pore diameter of the pores of the filter element of the device so that particles up to a desired, now larger pore diameter can pass through the filter element;
g) optionally filling the upper compartment of the receptacle of the device with a liquid that preferably does not contain any particles;
h) moving the liquid through the filter element, preferably by way of a means selected from the group consisting of centrifuge, pump, and combinations thereof;
i) isolating the liquid, including the now passed particles, from the lower compartment of the receptacle of the device;
j) optionally dissolving a reversible bond of particles to a coating of at least one filter element of the device, preferably by influencing the means for changing the pore diameter of the pores of the filter element; and
k) optionally repeating steps g) to j) until all particles of the liquid are present in separate liquids, separated according to size.

The method can be characterized in that the increase of the pore diameter of the pores of the filter element takes place by increasing a centrifugal speed of a centrifuge of the means for changing the pore diameter of the pores of the filter element.

Furthermore, the method can be characterized in that the increase of the pore diameter of the pores of the filter element takes place by decreasing an electrical voltage of a voltage source of the means for changing the pore diameter of the pores of the filter element.

According to the invention, additionally a use of the device according to the invention for separating particles of differing sizes present in a liquid is described. The use of the device can include isolating one or more blood cell fractions from blood, preferably for providing blood cell fractions for diagnostics and/or for producing blood products, in particular for creating cell therapeutics. Furthermore, the use of the device can be isolating bacterial cells from blood. In addition, the use of the device can be isolating exosomes from blood, serum or biosuspensions, preferably for providing exosomes for diagnostics and/or for producing vaccines (for example, liposomal vaccines). Apart from this, the use of the device can be isolating tissue cells from mixed tissue cell fractions. Moreover, the use of the device can be isolating cells from mixed cell suspensions originating from bioreactors, wherein the cells are preferably selected from the group consisting of plant cells, animal cells, human cells, bacterial cells, yeast cells, and combinations thereof.

The subject matter according to the invention shall be described in more detail based on the following figures and examples, without limiting the subject matter to the specific embodiments illustrated here.

FIG. 1 shows a first embodiment of a device according to the invention. The device comprises a receptacle 1 for receiving a liquid and at least one filter element 2 including a top surface 3, a bottom surface 4, and at least one side surface 5 connecting the top surface 3 to the bottom surface 4. The filter element 2 has through-pores 6 having a defined pore diameter. The filter element 2 is arranged in the receptacle 1 so as to divide the receptacle 1, in the direction of the top surface 3 of the filter element 2, into an upper compartment 7 and, in the direction of the bottom surface 4 of the filter element 2, into a lower compartment 8, so that particles of a liquid in the upper compartment 7 can only reach the lower compartment 8 if they pass through the filter element 2. The surface of the filter element 2 has an edge R and a center Z. The surface of the filter element 2 has an edge R and a center Z. The upper compartment 7 of the receptacle 1 has an opening 9 for receiving a liquid including particles. The device is characterized by comprising a means for changing the pore diameter of the pores 6 of the filter element 2. In this embodiment, this means comprises a centrifuge 20 and a body 11 for exerting a compression force or tensile force on the side wall 5 of the filter element 2, wherein here the body 11 is connected by way of a cord in a force-fit manner to an outer side of the at least one side surface 5 of the filter element 2, which is deflected by way of a deflection roller 12 provided on an attachment 13. An increasing centrifugal force of the centrifuge 20 brings about a stronger force on the body 11, and thus a stronger tensile force on the side wall 5 of the filter element 2, whereby the pores 6 of the filter element 2 widen.

Figure 2:
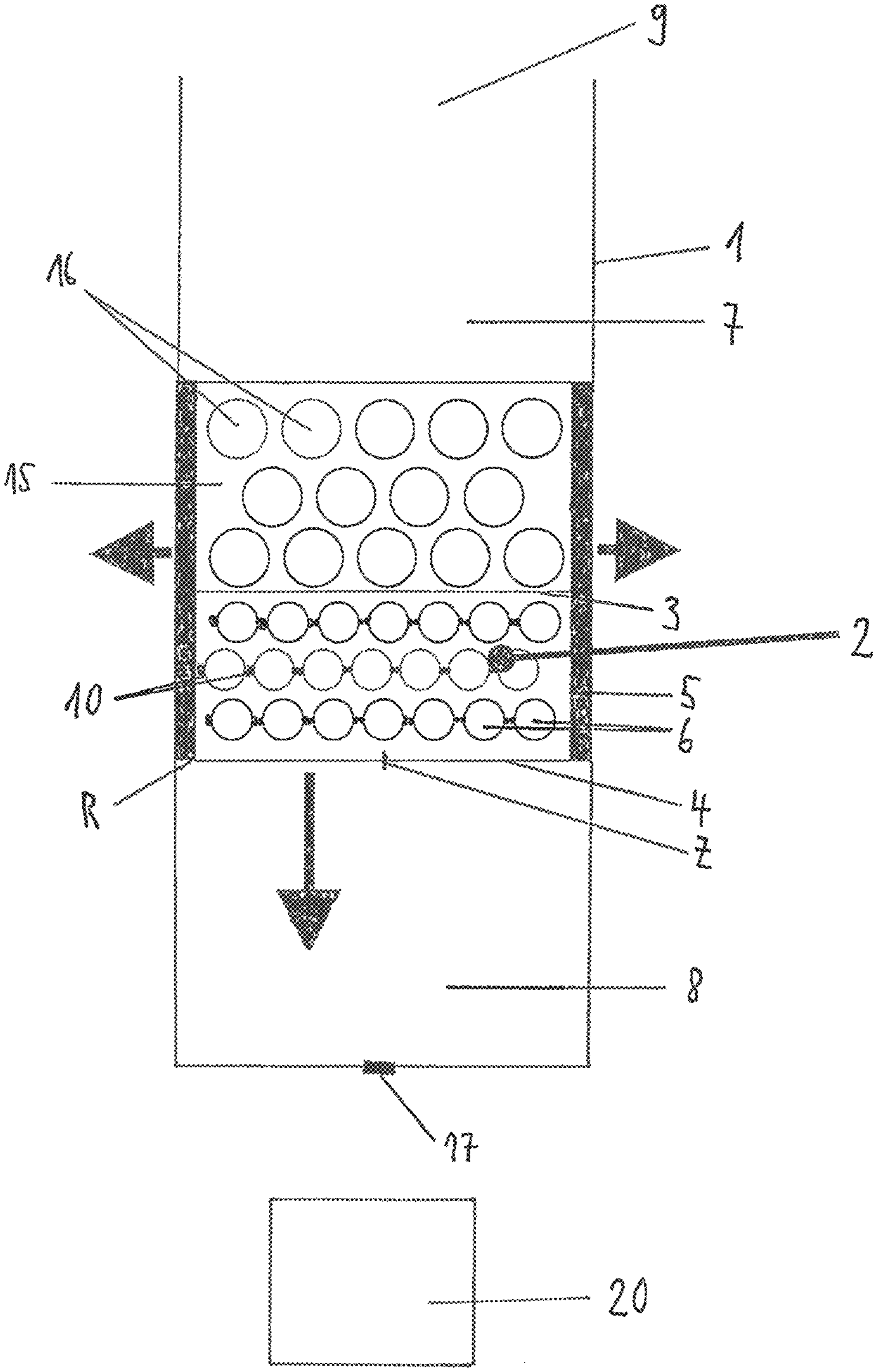

FIG. 2 shows a second embodiment of a device according to the invention. The device comprises a receptacle 1 for receiving a liquid and at least one filter element 2 including a top surface 3, a bottom surface 4, and at least one side surface 5 connecting the top surface 3 to the bottom surface 4. The filter element 2 has through-pores 6 having a defined pore diameter. The filter element 2 is arranged in the receptacle 1 so as to divide the receptacle 1, in the direction of the top surface 3 of the filter element 2, into an upper compartment 7 and, in the direction of the bottom surface 4 of the filter element 2, into a lower compartment 8, so that particles of a liquid in the upper compartment 7 can only reach the lower compartment 8 if they pass through the filter element 2. The surface of the filter element 2 has an edge R and a center Z. The upper compartment 7 of the receptacle 1 has an opening 9 for receiving a liquid including particles. The device is characterized by comprising a means for changing the pore diameter of the pores 6 of the filter element 2. In this embodiment, this means comprises a centrifuge 20 and at least two bodies 10 for exerting a compression force or tensile force on the pores of the filter element, wherein the at least two bodies 10 here are embodied as nanoparticles, which are arranged on opposing sides of the pores of the filter element. An increasing centrifugal force of the centrifuge 20 brings about a stronger force on the at least two bodies 10, and thus a stronger tensile force on the side edges of the pores 6 of the filter element 2, whereby the pores 6 of the filter element 2 widen.

Figure 3:
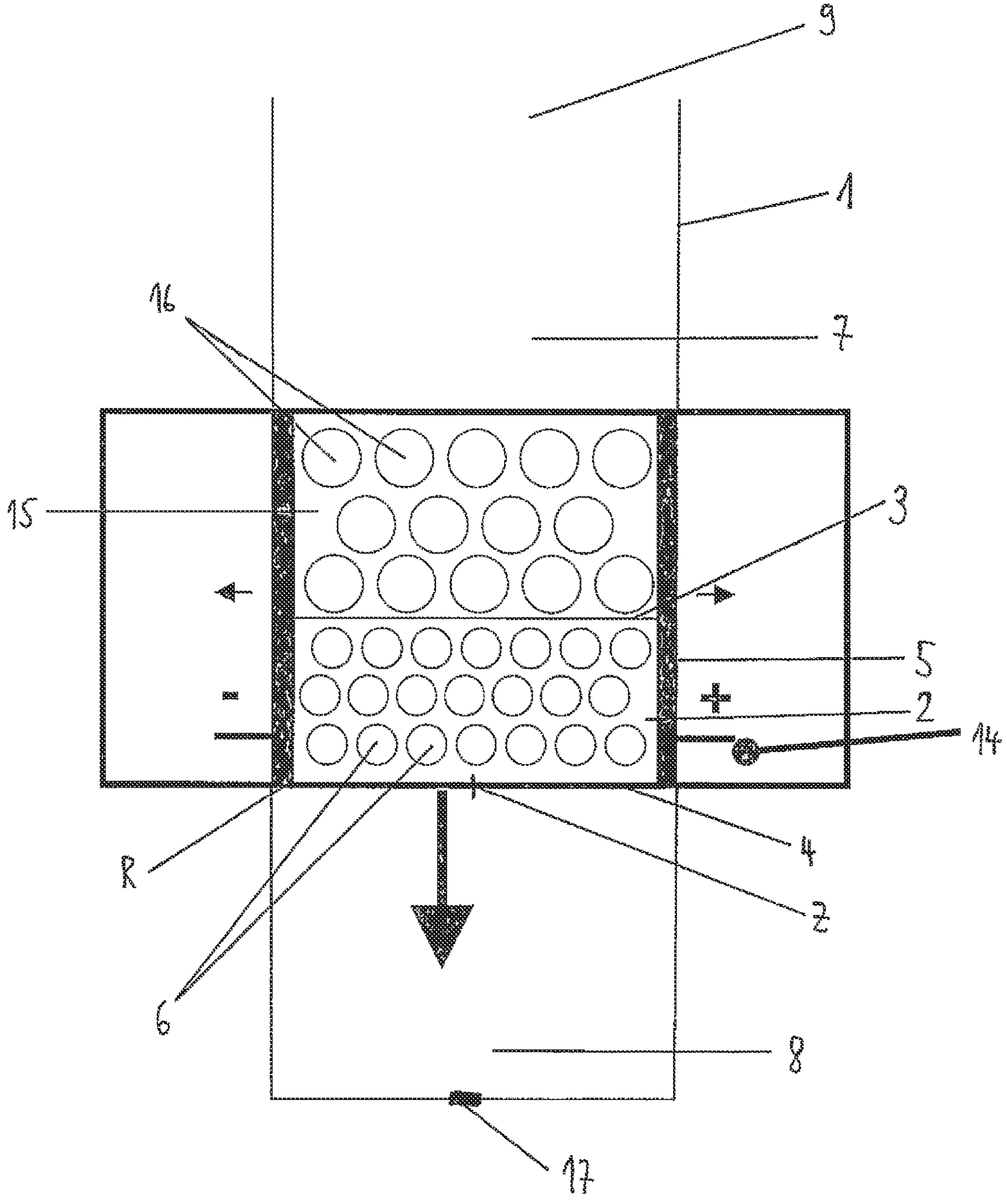

FIG. 3 shows a third embodiment of a device according to the invention. The device comprises a receptacle 1 for receiving a liquid and at least one filter element 2 including a top surface 3, a bottom surface 4, and at least one side surface 5 connecting the top surface 3 to the bottom surface 4. The filter element 2 has through-pores 6 having a defined pore diameter. The filter element 2 is arranged in the receptacle 1 so as to divide the receptacle 1, in the direction of the top surface 3 of the filter element 2, into an upper compartment 7 and, in the direction of the bottom surface 4 of the filter element 2, into a lower compartment 8, so that particles of a liquid in the upper compartment 7 can only reach the lower compartment 8 if they pass through the filter element 2. The surface of the filter element 2 has an edge R and a center Z. The upper compartment 7 of the receptacle 1 has an opening 9 for receiving a liquid including particles. The device is characterized by comprising a means for changing the pore diameter of the pores 6 of the filter element 2. In this embodiment, this means comprises an electrical voltage source 14 and at least one electrically conductive layer at the side wall 5 of the filter element 2. A decreasing electrical voltage of the electrical voltage source brings about a lower compression force on the side wall 5 of the filter element 2, whereby the pores 6 of the filter element 2 widen.

Figure 4:
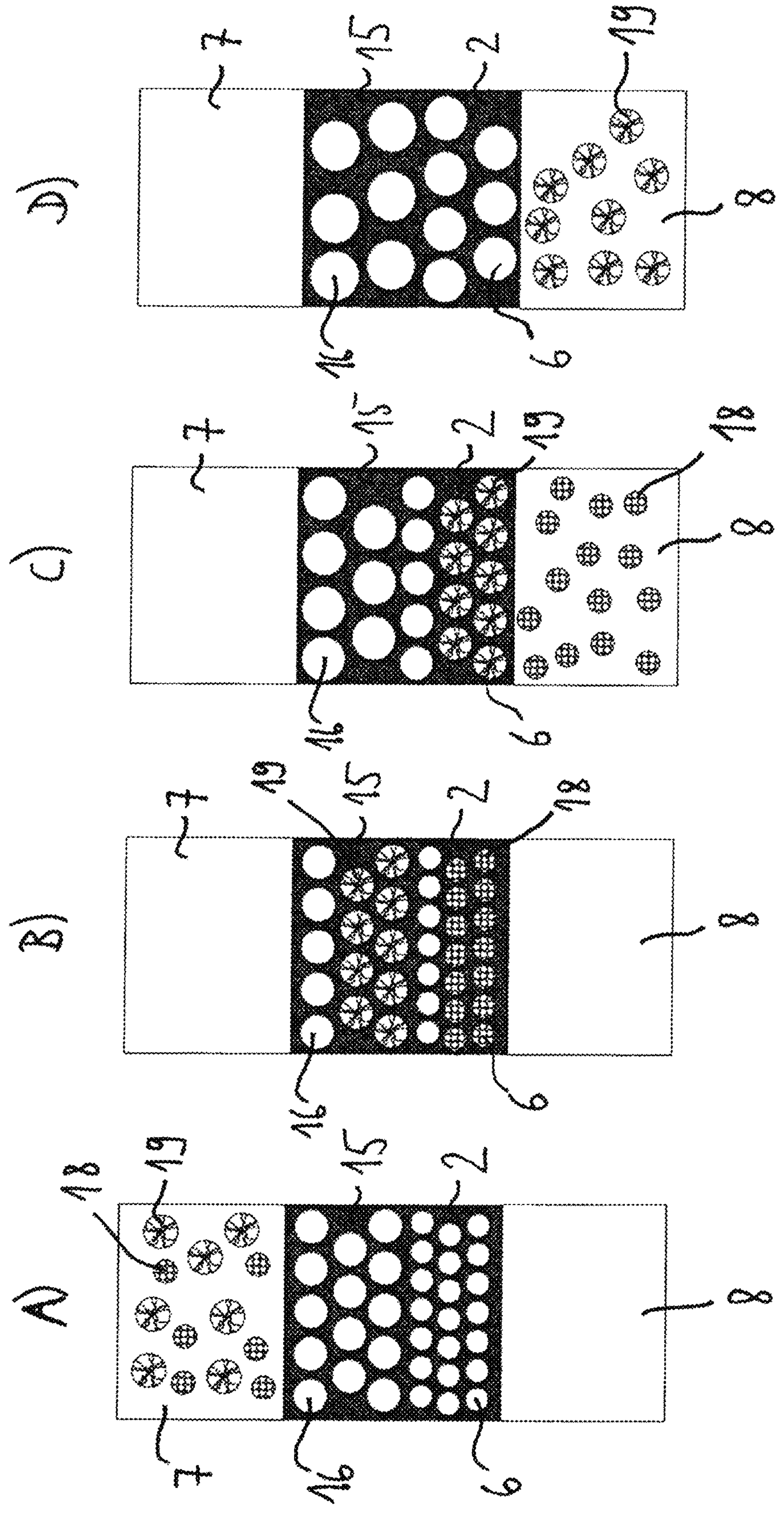

FIG. 4 schematically illustrates the separation of differently sized particles in a liquid by way of the device according to the invention, wherein the means for changing the pore width of the pores of the filter element comprises an electrical voltage source here, which is connected to at least one electrically conductive layer at the side surface of the filter element. No electrical voltage, or only a low electrical voltage, is applied to the electrically conductive layer, so as to keep the mean pore diameter of the pores 6 of the first filter element 2 and the pores 16 of the second filter element 15 as small as possible. A liquid (suspension) is added to the upper compartment 7 of the receptacle of the device, which contains a first group of particles 18 having a first size and a second group of particles 19 having a second size, the second size being larger than the first size (FIG. 4A). Using gravity or by way of the action of a centrifuge and/or pump, the first group of particles 18 passes through the second filter element 15 and reaches the first filter element 2 and is retained there, wherein the second group of particles 19 cannot reach the first filter element 2 and is already retained by the second filter element 15 (FIG. 4B). If the voltage applied by the electrical voltage source is now increased, the pores 6 of the first filter element 2 and the pores 16 of the second filter element 15 widen, so that the first group of particles 18 can pass through the first filter element 2 and is collected in the lower compartment 8 of the receptacle of the device, and the second group of particles 19 can reach the first filter element 2 and is retained there (FIG. 4C). After the liquid including the first group of particles 18 has been removed by a means 17 for withdrawing liquid from the lower compartment (for example, valve), the voltage applied by the electrical voltage source is further increased, so that the pores 6 of the first filter element 2 can widen even further, and now also the second group of particles 19 can pass through the first filter element 2 and is collected in the lower compartment 8 of the receptacle of the device (FIG. 4D). As a result, it is possible to incrementally separate the first group of particles 18 from the second group of particles 19.

EXAMPLE 1

Device Comprising a Centrifuge and at Least One Body for Changing the Pore Diameter In a first selection step, characterized by a first centrifugation acceleration, the liquid including particles that can pass through the pores of the filter element during the first centrifugal acceleration flows from the upper compartment into the lower compartment of the receptacle, while liquid including particles that cannot pass through the pores of the filter element under these conditions remains in the upper compartment of the receptacle. The liquid including particles, which is then located in the lower compartment, is removed from the lower compartment.

In a second selection step, a second centrifugal acceleration is applied, which is greater than the first centrifugal acceleration, whereby the action of the at least one body brings about an increase of the pore diameter of the pores of the filter element. As a result, liquid including larger particles can now pass through the filter element and be collected in the lower compartment of the receptacle, and can be isolated therefrom.

EXAMPLE 2

Device Comprising an Electrical Voltage Source for Changing the Pore Diameter In a first selection step, characterized by a electrical first voltage that is applied by way of the electrical voltage source, the liquid including particles that can pass through the pores of the filter element while the electrical voltage is present flows from the upper compartment into the lower compartment of the receptacle, while liquid including particles that cannot pass through the pores of the filter element under these conditions remains in the upper compartment of the receptacle. The liquid including particles, which is then located in the lower compartment, is removed from the lower compartment.

In a second selection step, an electrical voltage is applied, which is lower than the first electrical voltage, whereby an increase of the pore diameter of the pores of the filter element is brought about. As a result, liquid including larger particles can now pass through the filter element and be collected in the lower compartment of the receptacle, and can be isolated therefrom.

LIST OF REFERENCE NUMERALS

1: receptacle;
2: filter element;
3: top side of the filter element;
4: bottom side of the filter element;
5: side surface of the filter element;
6: through-pores of the filter element having a defined pore diameter;
7: upper compartment of the receptacle;
8: lower compartment of the receptacle;
9: opening of the upper compartment of the receptacle;
10: body for exerting a compression force or tensile force on the pores of the filter element;
11: body for exerting a compression force or tensile force on the side wall of the filter element;
12: deflection roller;
13: attachment of the deflection roller;
14 electrical voltage source;
15: second filter element;
16: through-pores of the second filter element having a defined pore diameter;
17: means for withdrawing liquid from the lower compartment (for example, valve);
18: first group of particles;
19: second group of particles, which are larger than the first group of particles;
20: centrifuge;
Z: center of a surface of the filter element;
R: edge of a surface of the filter element.

The invention claimed is:

1. A device configured for separating differently sized particles in a liquid, comprising:
a) a receptacle configured for receiving a liquid; and
b) at least one filter element, having a top surface, a bottom surface, and
at least one side surface connecting the top surface to the bottom surface,
wherein the at least one filter element includes through-pores having a defined pore diameter, and
wherein the at least one filter element is arranged in the receptacle so as to divide the receptacle, in the direction of the top surface of the at least one filter element, into an upper compartment and, in the direction of the bottom surface of the at least one filter element, into a lower compartment, so that particles of the liquid in the upper compartment can only reach the lower compartment if they pass through the at least one filter element, the upper compartment of the receptacle having an opening configured for receiving a liquid including particles, and
wherein the device comprises a means for changing the pore diameter of the pores of the at least one filter element,
wherein the means for changing the pore width of the pores of the at least one filter element comprises a centrifuge and
a) includes at least one body that is connected to an outer side of the at least one side surface of the at least one filter element in a force-fit manner, the at least one body being configured for exerting a compression force or tensile force on the at least one side surface of the at least one filter element by way of a change of the rotational speed of the centrifuge, so that the pores of the at least one filter element are compressed or expanded; or
b) includes at least one body which is arranged at the top side of the at least one filter element and/or in the at least one filter element, the at least one body being configured for exerting a compression force or tensile force on the pores of the at least one filter element by way of a change of the rotational speed of the centrifuge, so that the pores of the at least one filter element are compressed or expanded.

2. The device according to claim 1, wherein the means for changing the pore diameter of the pores of the at least one filter element is configured for exerting a force on the at least one filter element, which is either directed from the center of a surface of the at least one filter element toward the edges of this surface of the at least one filter element, or in an opposite direction.

3. The device according to claim 1, wherein the device comprises a control unit which is configured to control the means for changing the pore diameter of the pores of the at least one filter element.

4. The device according to claim 3, wherein the control unit is configured in such a way that
i) a centrifugal speed of a centrifuge of the means for changing the pore diameter of the pores of the at least one filter element is changed; and/or
ii) the pore diameter of the pores of the at least one filter element is changed in a range of 100 nm to 100 μm; and/or
iii) the pore diameter of the pores of the at least one filter element is incrementally changed, automatically over time or manually by input(s) of a user of the device, to a larger diameter.

5. The device according to claim 1, wherein the device includes "n" further filter elements, which are arranged on the at least one filter element in the direction of the upper compartment of the receptacle and which in each case have through-pores having a defined pore diameter, the defined pore diameter of the n filter elements being larger than the defined pore diameter of the at least one filter element and being larger for each of the n filter elements the closer the respective filter element is located in the direction of the upper compartment of the receptacle.

6. The device according to claim 5, wherein n is an integer ≥2.

7. The device according to claim 1, wherein the at least one filter element
i) comprises fibers that have through-pores; and/or
ii) comprises an elastic material having through-pores;
iii) comprises an electroactive material having through-pores;
iv) comprises a piezoelectric material having through-pores;
v) comprises a material that is selected from the group consisting of silicone elastomer, thermoplastic elastomer, magnetorheological elastomer, piezoelectric elastomer, thermoplastic urethane, and combinations thereof; and/or vi) comprises a composite material; and/or vii) comprises a woven fabric or knitted fabric; and/or viii) comprises a solid foam; and/or ix) has an expansion from the top side thereof to the bottom side thereof of >250 µm.

8. The device according to claim 1, wherein the at least one filter element of the device comprises a coating that is configured for reversibly binding particles of the liquid.

9. The device according to claim 8, wherein the coating i) comprises a material that is configured for being influenced by the means for changing the pore diameter of the pores of the filter element in such a way that the bond with the certain particles is dissolved; and/or ii) is arranged at the top surface, bottom surface and/or pore inner surface of the at least one filter element.

10. The device according to claim 1, wherein the lower compartment of the receptacle of the device comprises a means for withdrawing liquid from the lower compartment.

11. The device according to claim 1, wherein the receptacle is selected from the group consisting of centrifuge tubes, blood collection syringes, blood donation bags, culture bags for the biotechnological production of pharmaceuticals, bioreactor for biotechnological production, sample vessel, culture vessel, and combinations thereof.

12. The device according to claim 1, wherein the particles are selected from the group consisting of vesicles, virus particles, and biological cells.

13. A method for separating differently sized particles in a liquid, comprising:

a) providing a device according to claim 1;

b) adjusting the pore diameter of the pores of the at least one filter element of the device so that either no particles or only particles up to a desired particle diameter pass through the at least one filter element;

c) filling the upper compartment of the receptacle of the device with the liquid containing particles having differing sizes;

d) moving the liquid through the at least one filter element;

e) isolating the liquid from the lower compartment of the receptacle of the device;

f) increasing the pore diameter of the pores of the at least one filter element of the device so that particles up to a desired pore diameter can pass through the at least one filter element;

g) moving the liquid through the filter element; and h) isolating the liquid, including the passed particles, from the lower compartment of the receptacle of the device.

14. The method according to claim 13, wherein the pore diameter of the pores of the at least one filter element is increased by increasing a centrifugal speed of a centrifuge of the means for changing the pore diameter of the pores of the filter element.

15. The method according to claim 13, which includes i) isolating one or more blood cell fractions from blood, and/or ii) isolating bacterial cells from blood; and/or iii) isolating exosomes from blood, serum or biosuspensions; and/or iv) isolating tissue cells from mixed tissue cell fractions; and/or v) isolating cells from mixed cell suspensions originating from bioreactors.

16. A device configured for separating differently sized particles in a liquid, comprising:

a) a receptacle configured for receiving a liquid; and b) at least one filter element, having a top surface, a bottom surface, and at least one side surface connecting the top surface to the bottom surface, wherein the at least one filter element includes through-pores having a defined pore diameter, and wherein the at least one filter element is arranged in the receptacle so as to divide the receptacle, in the direction of the top surface of the at least one filter element, into an upper compartment and, in the direction of the bottom surface of the at least one filter element, into a lower compartment, so that particles of the liquid in the upper compartment can only reach the lower compartment if they pass through the at least one filter element, the upper compartment of the receptacle having an opening configured for receiving the liquid including particles, wherein the device comprises a means for changing the pore diameter of the pores of the at least one filter element, and wherein the at least one filter element of the device comprises a coating that is configured for reversibly binding particles of the liquid.

* * * * *